United States Patent
Christensen et al.

(10) Patent No.: US 7,481,972 B2
(45) Date of Patent: Jan. 27, 2009

(54) METHOD OF HEATING A PACKAGE

(75) Inventors: Aksel Christensen, Lomma (SE);
Tommy Ekström, Lund (SE); Tom Kjelgaard, Lund (SE); Anders Glemming, Hjärup (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 428 days.

(21) Appl. No.: 10/538,646

(22) PCT Filed: Dec. 11, 2003

(86) PCT No.: PCT/SE03/01929

§ 371 (c)(1),
(2), (4) Date: Jun. 10, 2005

(87) PCT Pub. No.: WO2004/056666

PCT Pub. Date: Jul. 8, 2004

(65) Prior Publication Data

US 2006/0051235 A1    Mar. 9, 2006

(30) Foreign Application Priority Data

Dec. 20, 2002    (SE) .................................. 0203862

(51) Int. Cl.
*A61L 2/07*    (2006.01)
(52) U.S. Cl. ............................ 422/1; 422/26
(58) Field of Classification Search .............. None
See application file for complete search history.

(56) References Cited

U.S. PATENT DOCUMENTS

| | | | |
|---|---|---|---|
| 3,511,169 A | 5/1970 | Fritzberg et al. | |
| 3,531,300 A | 9/1970 | Greenberg et al. | |
| 5,283,033 A | 2/1994 | Dodrill | |
| 2003/0053928 A1* | 3/2003 | Takano | 422/26 |
| 2005/0013908 A1* | 1/2005 | Persoons | 426/407 |

FOREIGN PATENT DOCUMENTS

| | | |
|---|---|---|
| EP | 1 015 324 B | 12/2002 |
| WO | WO 97/02140 A1 | 1/1997 |
| WO | 98/16431 A1 | 4/1998 |
| WO | 2005/016033 A | 2/2005 |

* cited by examiner

*Primary Examiner*—Elizabeth L McKane
(74) *Attorney, Agent, or Firm*—Buchanan, Ingersoll & Rooney PC

(57) ABSTRACT

The present invention relates to a method of heating a package, comprising the steps of: placing a number of packages in a retort, pressurising the retort to a first pressure by the supply of a gaseous pressurisation medium of low moisture content, supplying a heating medium for heating the package and the product packed in the package, raising, in connection with the supply of the heating medium, the pressure in the retort to a second pressure, and, during the final phase of the heat-treatment, reducing the pressure in the retort in such a manner that the pressure of the product packed in the package is higher than or equal to the pressure prevailing in the retort outside the package.

22 Claims, 1 Drawing Sheet

METHOD OF HEATING A PACKAGE

TECHNICAL FIELD

Figure 1:
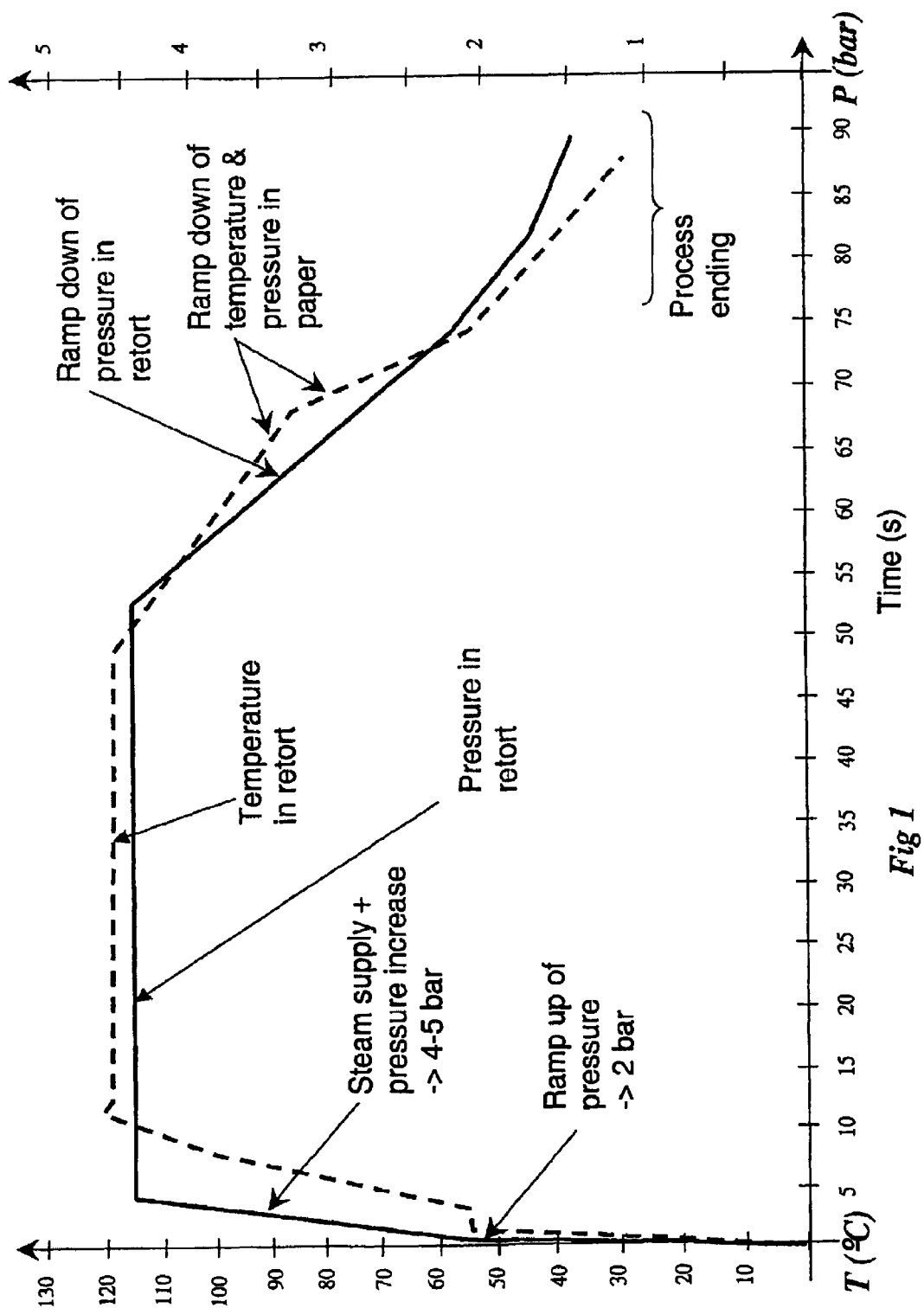

The present invention relates to a method of heat-treating a package. The method according to the present invention is particularly suitable for so-called retorting of packages of paper-based packaging laminate.

BACKGROUND ART

In order to extend the shelf life of a product, it is usual to heat-treat the product and its package. The selected level of heat-treatment depends, int. al., on the conditions under which the intention is to store the product packed in the package. A conventional method of carrying out shelf life-extending heat-treatment of a package and a food product filled into a package is so-called retorting.

Such a shelf life-extending heat-treatment of the packed food may suitably be put into effect using the method and under the conditions described in greater detail in International Patent Application carrying publication number WO98/16431 which is hereby incorporated as a reference. The packaging container is placed in a retort and heated therein with the aid of a first circulating gaseous medium, e.g. hot steam, to a temperature which in general lies within the range of 70-130° C. After a predetermined stay time at this selected temperature, the supply of the first gaseous medium is discontinued. Thereafter, the packaging container is cooled with a second circulating gaseous medium, for example cold air, and finally with a circulating liquid medium, for example cold water. The cooled packaging container is thereafter removed from the retort for further transport and handling. The total treatment time, including the time for heating up to and the time for cooling from the selected treatment temperature should be sufficient, in each individual case, to give the pertinent food a desired combination of a high F0-value and low C0-value. The expressions "F0-value" and "C0-value" are known to persons skilled in the art and related to the time (min.) which the food should need to be heated to a reference temperature (121° C.) to achieve the same level of sterility and the time the food would need, respectively, to be heated to a reference temperature (100° C.) to achieve the same level of cooking effect on all components of the food. It is obvious to a person skilled in the art that a higher treatment temperature in retorting gives a higher F0-value and a lower C0-value than a lower treatment temperature in a corresponding retorting during the same total treatment time, and that a retorting of the packed food should consequently be carried out at a relatively high treatment temperature within the range of 70-90° C. in order to achieve the desired combination of high F0-value and low C0-value.

Traditionally, this type of process is usually employed for packages of metal, glass or other materials possessing similar moisture barrier properties. Moreover, these packages are most generally relatively rigid, with the result that, during the retorting process, they are capable of withstanding quite powerful inner excess pressure from the product cooking in the closed package.

However, in recent times retorting of paper-based packaging laminate has been introduced. In order to withstand the retorting process, a number of variations of packaging laminates have been developed. One such packaging laminate is known from, for example, International Patent Application carrying publication number WO97/02140. The prior art packaging laminate has a rigid, but foldable core layer of paper or paperboard and outer, liquid-tight coatings of moisture and heat-resistant thermoplastic material on both sides of the core layer. In order to impart to the prior art packaging laminate tightness properties also against gases, in particular oxygen gas, the packaging laminate also displays a gas barrier, e.g. an aluminium foil, disposed between the core layer and the one outer coating.

From the prior art packaging laminate, retortable packaging containers are produced with the aid of packing machines of the type which, from a web or from prefabricated blanks of the packaging material, form, fill and seal finished packages in accordance with the so-called form/fill/seal technology.

From, for example, a flat folded tubular packaging blank of the prior art packaging laminate, retortable packaging containers are produced in that the packaging blank is first raised to an open, tubular packaging carton which is sealed at its one end by fold forming and sealing of the continuous, foldable end panels of the packaging carton for the formation of a substantially planar bottom seal. The packaging carton provided with a bottom is filled with the pertinent contents, for example a food, through its open end which is thereafter closed by an additional fold forming and sealing of the corresponding end panels of the packaging carton for the formation of a substantially planar top seal. The filled and sealed, normally parallelepipedic packaging container is thereafter ready for heat-treatment in order to impart to the packed food extended shelf life in the unopened packaging container.

However, it has proved that, in certain cases, problems may nevertheless arise in that the package absorbs liquid during the retorting process to such an extent that its mechanical properties are negatively affected. Above all, such problems arise at those portions where the packaging laminate displays open edges. These open edges are to be found in most parallelepipedic packages at a longitudinal joint which extends along the height of the package, and at both ends of the package. This problem is usually referred to as edge suction intake.

The above mentioned problem can, in certain cases, moreover be accentuated by the fact that paper-based packages often require a support pressure during the retorting process. The support pressure is the pressure which prevails in the retort and which balances the inner pressure which occurs because of the heating of the product in the closed package.

SUMMARY OF THE INVENTION

One object of the present invention is to realise a method of heat-treating a packaging material by means of which it is possible to retort packages of paper-based packaging laminate and avoid or at least reduce the so-called edge suction intake.

The above object has been attained according to the present invention by means of a method which comprises the steps of: placing a number of packages in a retort, pressurising the retort to a first pressure by the supply of a gaseous pressurising medium of low moisture content, supplying a heating medium for heating the package and the product packed in the package, raising, in connection with the supply of the heating medium, the pressure in the retort to a second pressure, and lowering the pressure during the final phase of the heat-treatment in the retort in such a manner that the pressure of the product packed in the package is higher than or equal to the pressure prevailing outside the package in the retort.

By controlling the pressure increases, supply of air and steam, as well as the pressure reductions in the above described method, it is possible to eliminate or at least greatly reduce edge suction intake. One probable explanation which at least partly explains how this is achieved is that, by supplying air under pressure before the packaging laminate is exposed to the moist heated steam, the pores in the edges of the paper-based material are filled with pressurised air. During the process, this pressurised air will take up the greater part of the spaces in which the steam would otherwise be capable of penetration. By controlling the pressure reduction in the retort during the pressure reduction phase so that the pressure in the retort is at any time slightly lower than the pressure in the pores of the packaging material, the charged air and possible steam which have penetrated into the pores will be forced out of the pores.

Preferred embodiments of the present invention are further apparent from the appended subclaims.

According to one preferred embodiment, said first pressure is at least approximately 1 bar, preferably approximately 2 bar, or even more preferably 3 bar. The higher the pressure before the steam is supplies, the lower will be the edge suction intake. However, in most commercially operating retorts, it is difficult to attain a pressure above approximately 2 bar before it is necessary to turn on some steam. Thus, the level to which it is possible to utilise the inventive concept as herein disclosed depends upon what type of retort is employed, but the important feature is to at least "charge" the pores with air up to a certain pressure level.

According to one preferred embodiment, said first pressure is approximately the same as said second pressure. By proceeding in this manner, it is in principle possible to obtain a gentle flow of air out through the pores of the package throughout the entire time of the retorting process.

Advantageously, said second pressure is of the order of magnitude of 3-6 bar, preferably approximately 4-5 bar. These pressures are selected considering that it is possible to be able to sterilise the product to a certain level and be possible to give the package sufficient support pressure during the retorting.

A simple method of supplying the requisite quantity of heat is to employ steam as the heating medium.

BRIEF DESCRIPTION OF THE ACCOMPANYING DRAWING

The present invention will now be described in greater detail hereinbelow, with reference to the accompanying schematic Drawing which, for purposes of exemplification, shows one currently preferred embodiment of the present invention. In the accompanying Drawing:

FIG. 1 shows in principle how pressure and temperature in the retort vary with time.

DETAILED DESCRIPTION OF ONE PREFERRED EMBODIMENT

In the following detailed description of one preferred embodiment, it should be taken into consideration that the selected level of the heat-treatment depends int. al. on those conditions under which the intention is to store the product packed in the package. Thus, different temperatures, stay times in the retort, pressure and other parameters are described in connection with different types of packages, products and storage conditions.

A conventional shelf life-extending heat-treatment of the packed food may suitably be put into effect in the manner and under the conditions described in greater detail in International Patent Application carrying publication number WO98/16431, which is hereby incorporated as reference. From this reference, it can be read how a conventional retorting process may be carried out. For purposes of clarity, this detailed description will largely be focused on the specific features which the present invention relates to. Those parts of the technical construction which are commercially available will not be described in greater detail, but reference is made instead to WO98/16431. The invention described in the foregoing may be employed for various types of retorts. For purposes of clarity, mention might be made of two main types of retorts together with which the present invention is intended to be employed, namely retorts with stationary product stands and retorts with rotating product stands. No detailed description of these types is needed, since both are commercially available, and since the inventive concept as herein disclosed may be employed for both types.

For further information as to how a packaging material which is adapted for retorting is constructed, reference is also to International Patent Application carrying publication number WO97/02140. This packaging laminate has a rigid, but foldable core layer of paper or paperboard and outer, liquid-tight coatings of moisture and heat-resistant thermoplastic material on both sides of the core layer. In order to impart to the prior art packaging laminate tightness properties also against gases, in particular oxygen gas, the packaging laminate moreover displays a gas barrier, for example an aluminium foil, disposed between the core layer and the one outer coating.

From this packaging laminate, retortable packaging containers are produced with the aid of packing and filling machines of the type which, from a web or from prefabricated blanks of the packaging laminate, form, fill and seal finished packages in accordance with the so-called form/fill/seal technology.

From, for example, a flat-folded tubular packaging blank of the prior art packaging laminate, retortable packaging containers are produced in that the packaging blank is first raised into an open, tubular packaging carton which is sealed at its one end by fold forming and sealing of the continuous foldable end panels of the packaging carton for the formation of a substantially planar bottom seal. The packaging carton provided with the bottom is filled with the pertinent contents, for example a food, through its open end which is thereafter sealed by an additional fold-forming and sealing of the corresponding end panels of the packaging carton for the formation of a substantially planar top seal. The filled and sealed, normally parallelepipedic packaging container is thereafter ready for heat-treatment in order to impart to the packed food extended shelf life in the unopened packaging container.

The thus obtained, filled packaging container is placed in a retort. Thereafter, the pressure in the retort is raised in that a pressure elevating medium in the form of air with low moisture content is supplied to the retort. The pressure in the retort is raised to a pressure of approx. 2 bar. Thereafter, the heating is commenced with the aid of a circulating gaseous heating medium, for example hot steam, to a temperature which in general lies within the range of 70-130° C. In the described preferred embodiment, steam is supplied at a temperature of the order of magnitude of 140° C. given that the temperature in the retort is kept at a temperature of 120° C.

Thereafter, compressed air continues to be admitted and hot steam is supplied so that the pressure in the retort is raised to approx. 4-5 bar. It takes approximately four minutes to reach this pressure level. It has proved that, in so-called rotating retorts, i.e. retorts with rotating product stands, approximately 5 bar is a suitable pressure, while, for retorts with stationary product stands, a suitable pressure is up to approximately 4 bar. These pressure levels are approximately 1-1.5 bar higher than the pressures which are needed in order that the support pressure prevent the packages from cracking because of the inner product pressure. However, it should be observed that these pressure levels depend upon the product, the type of package, the type of retort and the desired level of sterilisation. For example, the pressures may be varied between 3 and 6 bar with satisfactory results.

Simultaneously with the commencement of the supply of steam and while the product is kept warm, water is also supplied via nozzles to the outside of the packages. This is put into effect in order, in a rapid and simple manner, to distribute the warmth uniformly over the batch (all packages in the retort).

After a predetermined stay time at the selected temperature, the supply of the gaseous heating medium is discontinued. The packaging container is thereafter cooled using circulating liquid temperature-reducing medium, for example temperature controlled (colder) water. The cooled packaging container is thereafter removed from the retort for further transport and handling.

During this temperature reduction, the pressure is reduced in the retort according as the temperature falls. The pressure reduction is controlled so that the pressure in the pores of the packaging material throughout the entire cooling process is higher than or at least equal to the pressure prevailing in the retort on the outside of the packages.

By controlling the pressure increases, the inflows of air and steam, as well as the pressure reductions in the above described manner, it is possible to eliminate or at least greatly reduce edge suction intake. One probable explanation which at least partly goes some way to explaining how this is achieved is that by supplying air under pressure before the packaging laminate is exposed to the humid steam, the pores at the edges of the paper-based material are filled with pressurised air. During the process, this pressurised air will take up the greater part of the spaces in which the steam would otherwise be able to penetrate. By controlling the pressure reduction in the process in the retort so that the pressure in the retort at any time is slightly lower than the pressure in the pores of the packaging material, the charged air, and any possible steam which is penetrated into the pores, will be forced out of the pores.

Given the knowledge of the heat properties of the packaging material and the heat properties of the product, it is simple to calculate the pressure in the packages and the pressure in the pores of the packaging material by measuring the temperature on the outside of the packages. Alternatively, it is possible to test the relationship between the temperature of the coolant and the temperature of the packaging material in order, under normal operation of the retort, to measure the temperature of the coolant. The exact method of monitoring and controlling the process is highly dependent upon the type of retort which is employed and the commercial supplier of the retort used. Since this type of control of pressure and temperature in the retort and the media fed to the retort is available in commercially available retorts, this type of process control will not be described in greater detail here. Nor is the choice and design of process control of importance for carrying out the inventive concept as herein disclosed.

The only requirements which are placed for the sake of the inventive concept is that it is possible, initially, to supply air to a specific pressure and that, in the cooling, it is possible to reduce the pressure in a controlled manner so that the pressure may be reduced slightly more quickly than the pressure in the package and the consequential pressure in the pores in the packaging material.

As was mentioned earlier, the total treatment time, including the time for heating up to and the time for cooling from the selected treatment temperature should be sufficient in order, in each individual case, to give the pertinent food a desired combination of high F0-value and low C0-value. The expressions "F0-value" and "C0-value" are known to persons skilled in the art and relate to the time (min.) which the food should need to be heated at a reference temperature (121° C.) in order to achieve the same level of sterility and the time the food would need, respectively, to be heated at a reference temperature (1° C.) in order to achieve the same level of cooking effect on all component parts of the food.

As a result of the above-described process, it is possible to obtain a system where the pressure in the pores of the packaging material is higher than the pressure in the retort which, in turn, is higher than the pressure of the product against the package. The initial pressurisation by means of air entails that the pores will gain a head start in the pressurisation which then increases with the pressurisation and heating of the environment within the retort.

A person skilled in the art will readily perceive that many modifications of the embodiments of the present invention described herein are possible without departing from the scope of the invention as this is defined in the appended claims.

What is claimed is:

1. A method of heat-treatment of a package, comprising:
   placing a number of packages in a retort,
   pressurising the retort to a first pressure by the supply of a gaseous pressurisation medium with low moisture content,
   supplying a heating medium for heating the package and the product packed in the package,
   raising, in connection with the supply of the heating medium, the pressure in the retort to a second pressure, and
   reducing, during the final phase of the heat-treatment, the pressure in the retort in such a manner that the pressure in the packaging material and the pressure within the package is higher than or equal to the pressure prevailing in the retort outside the package.

2. The method as claimed in claim 1, wherein said first pressure is at least approximately 1 bar.

3. The method as claimed claim 2, wherein said second pressure is of the order of magnitude of 3 to 6 bar.

4. The method as claimed in claim 2, wherein said heating medium is steam.

5. The method as claimed in claim 2, comprising selecting, as package, a package of a paper-based packaging laminate.

6. The method as claimed in claim 1, wherein said second pressure is of the order of magnitude of 3 to 6 bar.

7. The method as claimed in claim 6, wherein said heating medium is steam.

8. The method as claimed in claim 7, comprising the step of selecting, as package, a package of a paper-based packaging laminate.

9. The method as claimed in claim 1, wherein said heating medium is steam.

10. The method as claimed in claim 9, further comprising supplying water via a number of nozzles to the outside of the packages.

11. The method as claimed in claim 10, wherein said second pressure is of the order of magnitude of 3 to 6 bar.

12. The method as claimed in claim 1, comprising selecting, as package, a package of a paper-based packaging laminate.

13. The method as claimed claim 12, wherein said second pressure is of the order of magnitude of 3 to 6 bar.

14. The method as claimed in claim 12, wherein said heating medium is steam.

15. The method as claimed in claim 1, wherein said first pressure is approximately 2 bar.

16. The method as claimed in claim 1, wherein said first pressure is approximately 3 bar.

17. The method as claimed in claim 1, wherein said second pressure is of the order of magnitude of approximately 4 to 5 bar.

18. The method as claimed in claim 1, wherein said gaseous pressurisation medium with low moisture content comprises air.

19. A method of heat-treatment of a package, comprising:
placing a number of packages in a retort,
pressurising the retort by the supply of a gaseous pressurisation medium with low moisture content,
supplying a heating medium for heating the package and the product packed in the package, and
reducing, during the final phase of the heat-treatment, the pressure in the retort in such a manner that the pressure in the packaging material and the pressure within the package is higher than or equal to the pressure prevailing in the retort outside the package.

20. The method as claimed in claim 19, wherein said heating medium is steam.

21. The method as claimed in claim 19, comprising selecting, as package, a package of a paper-based packaging laminate.

22. The method as claimed in claim 19, wherein said gaseous pressurisation medium with low moisture content comprises air.

* * * * *